US010191048B2

(12) United States Patent
Kveder et al.

(10) Patent No.: US 10,191,048 B2
(45) Date of Patent: Jan. 29, 2019

(54) FLUOROMETRIC IMMUNOASSAY FOR DETECTION OF ANTI-DSDNA ANTIBODIES

(71) Applicant: UNIVERZITETNI KLINICNI CENTER LJUBLJANA, Ljubljana (SI)

(72) Inventors: Tanja Kveder, Ljubljana (SI); Katja Lakota, Kranj (SI); Tinka Svec, Domzale (SI); Sasa Cucnik, Ljubljana (SI); Polona Zigon, Male Braslovce (SI); Ales Ambrozic, Domzale (SI); Snezna Sodin-Semrl, Kranj (SI); Borut Bozic, Ljubljana (SI); Matija Tomsic, Ljubljana Sentvid (SI)

( * ) Notice: Subject to any disclaimer, the term of this patent is extended or adjusted under 35 U.S.C. 154(b) by 131 days.

(21) Appl. No.: 15/116,355

(22) PCT Filed: Feb. 3, 2015

(86) PCT No.: PCT/SI2015/000003
§ 371 (c)(1),
(2) Date: Aug. 3, 2016

(87) PCT Pub. No.: WO2015/119582
PCT Pub. Date: Aug. 13, 2015

(65) Prior Publication Data
US 2016/0349255 A1    Dec. 1, 2016

(30) Foreign Application Priority Data
Feb. 4, 2014   (SI) .................. 201400043

(51) Int. Cl.
G01N 33/564    (2006.01)
G01N 33/68     (2006.01)

(52) U.S. Cl.
CPC ....... G01N 33/564 (2013.01); G01N 33/6854 (2013.01); G01N 2800/104 (2013.01); G01N 2800/56 (2013.01)

(58) Field of Classification Search
None
See application file for complete search history.

(56) References Cited

U.S. PATENT DOCUMENTS

| | | |
|---|---|---|
| 4,690,905 A | 9/1987 | Diamond |
| 5,700,641 A | 12/1997 | Salonen |
| 2013/0149700 A1 | 6/2013 | Weber et al. |

FOREIGN PATENT DOCUMENTS

| | | |
|---|---|---|
| WO | 9627131 | 9/1996 |

OTHER PUBLICATIONS

1. NOVA Lite (dsDNA antibody analysis kit, 2011). (Year: 2011).*
Paithankar et al. (Nucleic Acids Res 1991 vol. 19, No. 6, total 1 page). (Year: 1991).*
Domljanovic et al., "Complexes of DNA with fluorescent dyes are effective reagents for detection of autoimmune antibodies", Scientific Reports, May 15, 2017; 7(1):1925. doi: 10.1038/s41598-017-02214-0; 9 pgs.
Riboldi et al., "Statins and autoimmune diseases", Autoimmunity, vol. 14 issue: 9, pp. 765-768, Sep. 1, 2005.
Shovman et al., "Multiplexed AtheNA multi-lyte immunoassay for ANA screening in autoimmune diseases", Autoimmunity, 38(1):105-109, Feb. 2005.
López-Hoyos et al., "Clinical disease activity and titers of anti-dsDNA antibodies measured by an automated immunofluorescence assay in patients with systemic lupus erythematosus", Lupus, 14(7):505-509, Jul. 1, 2005.
Radice et al., "A new oligonucleotide-based ELISA for the detection of anti-double-stranded DNA antibodies", Autoimmunity, 39(2), pp. 113-119, Mar. 2006.
Jaekell et al., "Anti-dsDNA antibody subtypes and anti-C1q antibodies: toward a more reliable diagnosis and monitoring of systemic lupus erythematosus and lupus nephritis", Lupus, 15(6):335-345, 2006.
Yu et al., "Anti-dsDNA Antibody Assay: High Specificity and Sensitivity with a Filtration Radioassay in Comparison to Low Specificity with the Standard ELISA" Journal of Rheumatology, 34:4, pp. 734-739, 2007.
Bardin et al., "BioPlex™ 2200 multiplexed system: Simultaneous detection of anti-dsDNA and anti-chromatin antibodies in patients with systemic lupus erythematosus", Autoimmunity, 42:1, pp. 63-68, Jul. 7, 2009.
McCloskey et al., Journal of Clinical Laboratory Analysis, 2010.
Fiegel et al., "Autoantibodies to double-stranded DNA—intermethod comparison between four commercial immunoassays and a research biosensor-based device", Lupus, 19(8), pp. 957-964 Jul. 2010.
Biesen et al.,"Anti-dsDNA-NcX ELISA: dsDNA-loaded nucleosomes improve diagnosis and monitoring of disease activity in systemic lupus erythematosus", Arthritis Research & Therapy, 13(1): R26, 9 pgs, Feb. 10, 2011.
(Continued)

Primary Examiner — Changhwa J Cheu
(74) Attorney, Agent, or Firm — Gina M. Lupino

(57) ABSTRACT

The present invention relates to the field of immunological methods, more precisely to the field of detection methods for antibodies against double-stranded DNA (dsDNA) for diagnostics of chronic autoimmune diseases, such as systemic lupus erythematosus (SLE). The fluorometric immunoassay method for detection of anti-dsDNA solves the technical problem of designing a method for detection of the aforesaid antibodies, which would be faster, cheaper and less toxic as the standard Farr-RIA method, but would have the same diagnostic specificity (which is 100%) and improved diagnostic sensitivity (for 3%). Detection of anti-dsDNA is based on detection of fluorescence in two fractions of samples, in the supernatant and in the sample with a precipitate, which contains immune complexes composed of added dsDNA and anti-dsDNA present in the patient's serum, wherein the detected fluorescence is a consequence of binding fluorescent dyes with dsDNA bound in the complexes or with free dsDNA. The method according to the invention allows obtaining reliable results, fast sample analysis and results availability to the attending physician, use of human and environmentally safe chemicals and lowering of costs in comparison to the standard Farr-RIA method.

11 Claims, 1 Drawing Sheet

(56) References Cited

OTHER PUBLICATIONS

Ghirardello et al., "Diagnostic accuracy of currently available anti-double-stranded DNA antibody assays. An Italian multicentre study", Clinical and Experimental Rheumatology, 29(1), pp. 50-56, Jan.-Feb. 2011.

Urowitz et al., "Autoantibody response to adjuvant and nonadjuvant H1N1 vaccination in systemic lupus erythematosus", Arthritis Care & Research, vol. 63, No. 11, pp. 1517-1520, Nov. 2011.

Miyawaki et al., "The effect of methotrexate on improving serological abnormalities of patients with systemic lupus erythematosus", Modern Rheumatology, vol. 23, Issue 4, pp. 659-666, Jul. 2013.

Rose et al., "IFNα and its response proteins, IP-10 and SIGLEC-1, are biomarkers of disease activity in systemic lupus erythematosus", Annals of the Rheumatic Diseases, 72(10), pp. 1639-1645, Oct. 2013.

Venner et al., "Comparison of three anti-dsDNA assays: Performance and correlation with systemic lupus erythematosus disease activity", Clinical Biochemistry, vol. 46, Issue 4-5, pp. 317-320, Mar. 2013.

Hillebrand et al., "Changes in Farr radioimmunoassay and EliA fluorescence immunoassay anti-dsDNA in relation to exacerbation of SLE", Lupus, vol. 23, pp. 1169-1173, Aug. 8, 2013.

Pincus et al., "Measurement of Serum DNA-Binding Activity in Systemic Lupus Erythematosus", The New England Journal of Medicine, No. 281, pp. 701-705, Sep. 25, 1969.

Slater et al., "The Crithidia luciliae kinetoplast immunofluorescence test in systemic lupus erythematosus", Clinical & Experimental Immunology, vol. 25(3), pp. 480-486, 1976.

Blount et al., "Reactive oxygen species modify human DNA, eliciting a more discriminating antigen for the diagnosis of systemic lupus erythematosus", Clinical & Experimental Immunology, vol. 81, pp. 384-389, 1990.

Salingue-Canonne et al., "Detection of anti-DNA antibodies for the diagnosis of disseminated lupus erythematosus. Comparative study of immunoenzyme methods and a Farr test", Pathologie Biologie, vol. 49(8), Oct. 2001, Paris, France.

Suh-Lailam et al., "Evolution of a high avidity anti-dsDNA IgG enzyme-linked immunosorbent assay for the diagnosis of systemic lupus erythematosus", International Journal of Clinical and Experimental Pathology, vol. 4(8), pp. 748-754, 2011.

Žigon et al., Comparison and evaluation of different methodologies and tests for detection of anti-dsDNA antibodies on 889 Slovenian patients'and blood donors' sera, Croatian Medical Journal, vol. 52(6), pp. 694-702, Dec. 2011.

Bjorkman et al., "The use of fluorometric assays to assess the immune response to DNA in murine systemic lupus erythematosus", Scandinavian Journal of Immunology, vol. 57(6), pp. 525-533, Jun. 2003.

Jiang et al., "The expression of plasma nucleosomes in mice undergoing in vivo apoptosis", Clinical Immunology, vol. 106(2), pp. 139-147, Feb. 2003.

Chen et al., "Sensitive detection of plasma/serum DNA in patients with systemic lupus erythematosus", Autoimmunity, vol. 40(4), pp. 307-310, Jun. 2007.

International Search Report relating to priority application PCT/SI2015/000003, dated Apr. 27, 2015.

Lindorfer et al., "A bispecific dnDNA x monoclonal antibody construct for clearance of anti-dsDNA IgG in systemic lupus erythematosus", Journal of Immunological Methods, Elsevier Science Publishers B.V., vol. 248, No. 1-2, pp. 125-138, Jan. 1, 2001, Amsterdam, NL.

Neogi et al., "Anti-dsDNA antibody test by Farr and ELISA techniques is not equivalent", Journal of Rheumatology, vol. 33 (9), pp. 1785-1788, Sep. 2006.

Launay et al., "Comparison of the Farr radioimmunoassay, 3 commercial enzyme immunoassays and Crithidia luciliae immunofluorescence test for diagnosis and activity assessment of systemic lupus erythematosus", Clinica Chemica Acta, Elsevier BV, vol. 411, No. 13-14, pp. 959-964, Jul. 4, 2010, Amsterdam, NL.

Nn, "Quanta Lite HA dsDNA ELISA", Aug. 8, 2011, URL: http://www.inovadx.com/PDF/clsi/704615clsi_EN.pdf, San Diego, CA.

Nn, "Instructions for Use. Farrzyme(TM) Human high avidity anti-dsDNA Enzyme Immonuoassay Kit MK072", Dec. 11, 2008, pp. 1-13, URL: http://www.inovadx.com/PDF/di/MK072_EN.pdf, Birmingham, UK.

Tong et al., "[The comparison of the three anti-dsDNA antibofy detecting test].", Zhonghua Shi Yan He Linchuang Bing Du Xue Za Zhi = Zhonghua Shiyan He Lingchuang Bingduxue Zazhi = Chinese Journal of Experimental and Clinical Virology, vol. 23, No. 1, pp. 74-75, Feb. 2009.

Chiaro et al., "Significant differences in the analytic concordance between anti-dsDNA IgG antibody assays for the diagnosis of systemic lupus erythematosus-Implications for inter-laboratory testing", Clinica Chimica Acta, vol. 412, No. 11-12, pp. 1076-1080, May 1, 2011.

Antico et al., "Diagnosing systemic lupus erythematosus: new generation immunoassays for measurement of anti-dsDNA antibodies are an effective alternative to the Farr technique and the Crithidia luciliae immunofluorescence test", Lupus, vol. 19(8), pp. 906-912, Jul. 2010.

Derksen et al., "A comparison between the Farr radioimmunoassay and a new automated fluorescence immunoassay for the detection of antibodies against double stranded DNA in serum", Annals of the Rheumatic Diseases, vol. 61, No. 12, pp. 1099-1102, Dec. 1, 2002.

Villalta et al., "Evolution of a new automated enzyme fluoroimmunoassay using recombinant plasmid dsDNA for the detection of anti-dsDNA antibodies in SLE", Journal of Clinical Laboratory Analysis, vol. 16, No. 5, pp. 227-232, Jan. 1, 2002.

Crowley-Nowick et al., "Polyethylene glycol precipitates of serum contain a large proportion of uncomplexed immunoglobulins and C3", Immunological Investigations 1996, Jan.-Mar. vol. 25, No. 1-2, pp. 91-101, Jan. 1996.

Wold et al, "Deoxyribonucleic Acid Antibody: A Method to Detect Its Primary Interaction with Deoxyribonucleic Acid", Science, vol. 161, No. 3843, pp. 806-807, Aug. 23, 1968.

* cited by examiner

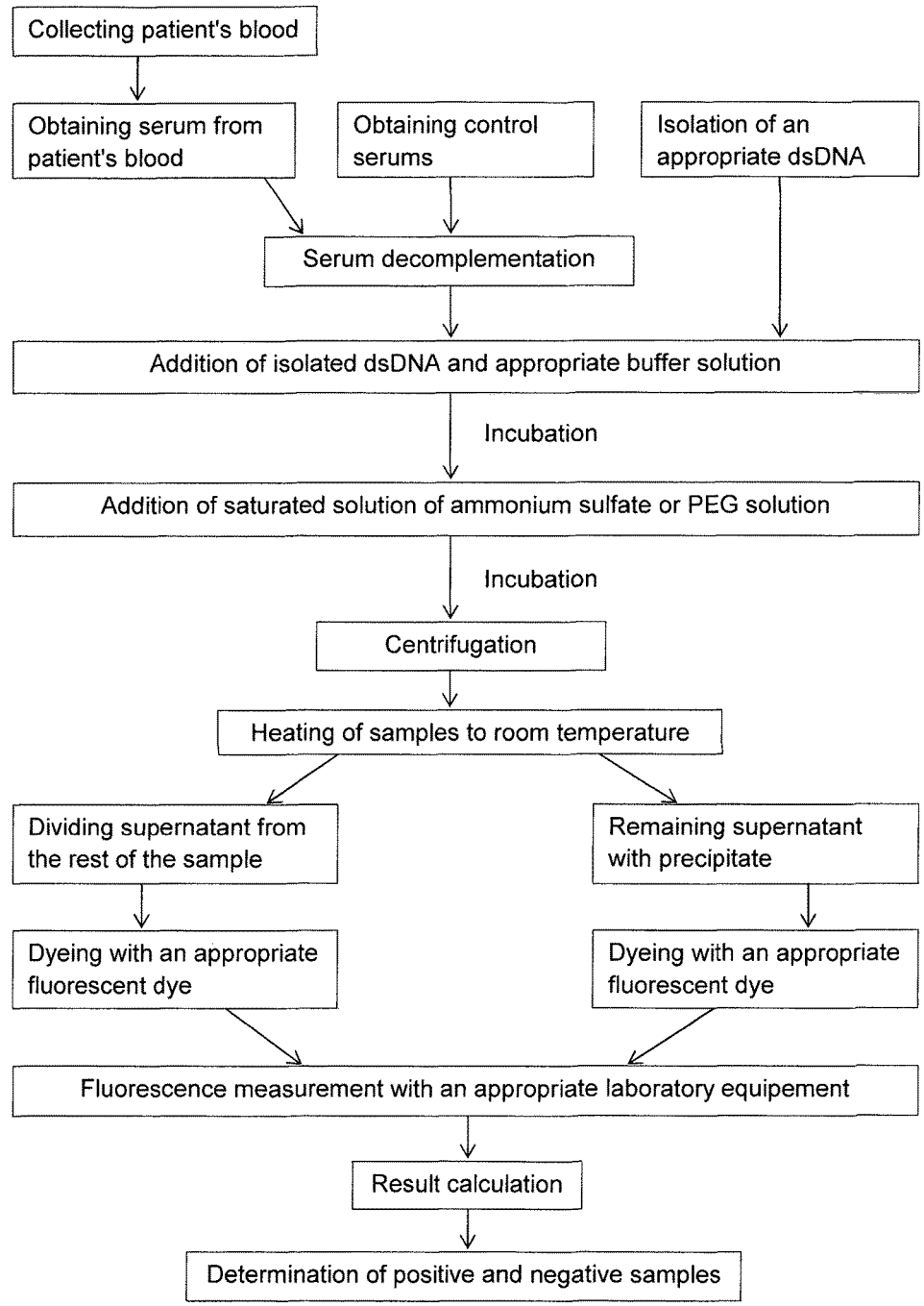

FLUOROMETRIC IMMUNOASSAY FOR DETECTION OF ANTI-DSDNA ANTIBODIES

FIELD OF INVENTION

The present invention relates to the field of immunological methods, more precisely to the field of detection methods for antibodies against double-stranded DNA (dsDNA) for diagnostic purposes of chronic autoimmune diseases, such as systemic lupus erythematosus (SLE).

TECHNICAL PROBLEM

SLE is a chronic autoimmune disease with an incidence among the general population between 4 to 250 patients per 100000 persons. This disease can affect any part of the body, however skin, joints, kidneys, lungs, heart and nervous system is are among the most commonly affected. Antibodies against double-stranded DNA (anti-dsDNA) were discovered in 1957 and it was observed that they are present in 70 to 80% of patients, when the disease was active. Due to the presence of the aforementioned antibodies in blood and tissues, immune complexes dsDNA/anti-dsDNA are formed in the blood, as well as in tissues. Their removal is impaired because of the decreased number and reduced function of receptors, which consequently causes inflammation and tissue damage. Anti-dsDNA antibodies are used as one of the diagnostic criteria for SLE. Values of anti-dsDNA measured in patient's serum are also used for monitoring disease activity and predicting disease worsening, as the amount of anti-dsDNA correlates with SLE activity. Their quantity is significantly increased in the acute phase of the disease. In addition, increased amounts of anti-dsDNA may occur prior to disease aggravation, even more than one year in advance.

Laboratory diagnostics are very important, as the signs and symptoms of SLE are extremely variable and are often similar to symptoms of other diseases. Anti-dsDNA in serum can be detected using different techniques and methods. The golden standard is a radioimmune method according to Farr (Farr-RIA), in which the presence of anti-dsDNA in the patient's serum is measured with radioactively labelled bacterial, bacteriophage or human dsDNA. Presence of anti-dsDNA in the patient's serum is determined with the ratio of radioactive dsDNA bound in complexes with anti-dsDNA and total radioactivity of the added dsDNA.

The main problem of the Farr-RIA method is the use of expensive radioactive, toxic and carcinogenic reagents, which represent a threat to our health and the environment.

Alternative methods for the detection of anti-dsDNA, such as indirect immunofluorescence and enzyme-linked immunosorbent assay on a solid carrier (ELISA), are not very suitable for routine diagnostics, as they are less diagnostically specific and more sensitive, which results in more false-positive results. In addition, the results cannot be correlated to disease activity. The semi-quantitative immunofluorescent test with protist Crithidia luciliae (CLIFT) is commonly used as a first-level method. Consequently, additional testing of positive results has to be done with Farr-RIA method in order to eliminate clinically useless positive results. Correlation of anti-dsDNA with disease activity is much better in Farr-RIA than in the CLIFT method, as the latter is only qualitative or semi-quantitative at best.

In the past years numerous authors have suggested several different methods for laboratory diagnostics of SLE, in which anti-dsDNA detection is replaced, for example with monitoring of gene expression, determination of marker nucleotide sequences or determination of activities of different biomarkers, which are usually enzymes or components of the immune system. Despite development of alternative methods, routine diagnostics is still based on detection of anti-dsDNA and it therefore seems reasonable to develop and upgrade already known and clinically useful methods.

The technical problem, which is solved by the present invention, is designing a method for detection of anti-dsDNA, which will be based on the principles of standard radioimmune Farr-RIA method, but will differ in the used materials and chemicals which will be nontoxic for humans and the environment. The new method should have at least the same sensitivity, specificity and reproducibility as the standard radioimmune method or other alternative diagnostic methods. In addition, the new method should be better priced, which is one of the key factors in routine diagnostics.

STATE OF THE ART

In 1969 Pincus et al. published an article entitled » Measurement of Serum DNA-Binding Activity in Systemic Lupus Erythematosus« (N Engl J Med), in which a radioimmune method for detection of anti-dsDNA was described, which was diagnostically effective for SLE diagnostics. This method is based on the precipitation of immune complexes, which are formed after incubation of patient's serum with radioactively labelled bacterial, bacteriophage, calf (calf thymus) or human dsDNA. Immune complexes are precipitated with ammonium sulfate, since it changes the solubility of molecules. Result reading in the Farr-RIA method is based on the determination of the ratio between measured radioactivity of the supernatant and measured radioactivity of the sample with precipitate, which increases due to precipitated immune complexes.

In 1976 Slater et al. published an article entitled » The Crithidia luciliae kinetoplast immunofluorescence test in systemic lupus erythematosus« (Clin Exp Immunol), in which the CLIFT technique was described. According to the authors, this method allows for the detection of anti-dsDNA presence in the patient's serum, as the protist Crithidia luciliae has a kinetoplast with high concentrations of dsDNA, but lacks other antigens, thereby enabling high method specificity. A molecule labelled with a fluorochrome, which will bind to antibodies, is added to the prepared samples.

Kinetoplast fluorescence as detected under the fluorescent microscope represents a positive result. As a consequence of this finding, several commercially available kits for anti-dsDNA detection were prepared.

The ELISA method has been known for years and has several different applications including diagnostics for numerous diseases, including autoimmune diseases. It includes five steps. The antigen is bound to a solid carrier, then, the free binding sites are blocked, followed by the addition of primary antibodies, which are detected with secondary antibodies labelled with chromogenic, fluorogenic or chemiluminiscent reporter, which allows spectrophotometric detection after substrate addition. Several commercial ELISA kits for anti-dsDNA detection are available (Quanta Lite dsDNA, INOVA; Anti-dsDNA DIASTAT, EURO DIAGNOSTICA), which include dsDNA from calf thymus, as the antigen. Some of the commercial kits use plasmid DNA. Blount et al. (Reactive oxygen species modify human DNA, eliciting a more discriminating antigen for the diagnosis of systemic lupus erythematosus, Clin Exp Immunol, 1990) increased the diagnostic sensitivity and specificity of ELISA tests with the use of denaturated DNA in laboratory diagnostics of SLE. Low and high avidity anti-dsDNA can be detected with this method.

Telomeric DNA can be used as an antigen for anti-dsDNA detection. This is known from patents WO9627131 and U.S. Pat. No. 5,700,641. Telomeric sequences are included in diagnostic kits or pharmaceutical compositions for inhibition or decrease of anti-dsDNA activity in order to treat patients.

According to patent U.S. Pat. No.4,690,905 monoclonal antibodies against human anti-dsDNA are known, which can be used for determination of presence of human anti-dsDNA in serum or for elimination of aforesaid antibodies in SLE patients. The detection method can be radioimmune, enzyme-immune, immunofluorescent or any other appropriate method.

A decade ago commercially available fluorescent immune method (EliA dsDNA, Pharmacia Diagnostics, Germany) was developed. This method is based on the detection of immune complexes, which have formed after recognition of plasmid DNA bound to a solid carrier by antibodies characteristic for a specific autoimmune disease. Immune complexes are detected with secondary antibodies linked to an enzyme, which enables fluorescent detection after addition of a substrate.

Several studies and comparisons of the above mentioned methods were made in order to analyse their diagnostic usefulness. It was found that the most reliable method is the standardized Farr-RIA method, while according to results of Salingue-Canonne et al. (*Detection of anti-DNA antibodies for the diagnosis of disseminated lupus erythematosus. Comparative study of immunoenzyme methods and a Farr test, Pathol Biol (Paris)*, 2001) and Suh-Lailam et al. (*Evaluation of a high avidity anti-dsDNA IgG enzyme-linked immunosorbent assay for the diagnosis of systemic lupus erythematosus, Int J Clin Exp Pathol,* 2011) ELISA and other enzyme-immune methods, despite improvements do reach high enough analytic specificity. The Farr-RIA method is also better than fluorescent immune test EliA dsDNA. igon et al. (*Comparison and evaluation of different methodologies and tests for detection of anti-dsDNA antibodies on 889 Slovenian patients' and blood donors' sera, Croat Med J,* 2011) have reported that CLIFT method may be used as the primary test, which excludes all negative samples and thereby decreases the number of performed Farr-RIA tests. It is a general opinion that it would be useful to improve the Farr-RIA method so that harmful chemicals to health and environment are avoided.

Such attempts date back to year 2003, when Bjorkman et al. have published an article entitled »*The use of fluorometric assays to assess the immune response to DNA in murine systemic lupus erythematosusa* « (*Scand J Immunol*). In this article, they report on immunopathogenic studies of SLE induced in mice, whereby the amounts of free DNA, immune complex bound DNA and free anti-DNA were determined. Immune complexes were precipitated with ammonium sulfate as in the Farr-RIA method. The concentration of dsDNA was measured with the commercially available dye PicoGreen on the basis of a calibration curve. The same dye was also used for dsDNA concentration measurements by Jiang et al. (*The expression of plasma nucleosomes in mice undergoing in vivo apoptosis, Clinical Immunol,* 2003) and Chen et al. (*Sensitive detection of plasma/serum DNA in patients with systemic lupus erythematosus, Autoimmunity,* 2007).

SOLUTION OF THE TECHNICAL PROBLEM

The essence of the fluorometric immunoassay (FIA) method for detection of anti-dsDNA for diagnostics of autoimmune diseases, especially SLE, as per invention, is in that, it is based on the detection of fluorescence in two fractions of samples, that is in the supernatant and in the sample with the pellet, which contains immune complexes of dsDNA and anti-dsDNA, wherein the detected fluorescence is a consequence of the binding of fluorescent dyes to dsDNA.

The FIA method includes the following steps:
a. obtaining and decomplementation of patient's serum and control serums;
b. isolation of dsDNA from an appropriate source;
c. addition of isolated dsDNA from step b together with an appropriate buffer solution to decomplemented serums;
d. warm incubation of the mix from step c, followed by a cold incubation;
e. precipitation of immune complexes formed in step d with a saturated solution of ammonium sulfate or a solution of polyethylene glycol (PEG);
f. separation of precipitated immune complexes from unbound dsDNA with centrifugation;
g. heating of samples to room temperature;
h. labelling of the supernatant and the sample with the precipitate from step f with an appropriate fluorescent dye;
i. measurement of sample fluorescence;
j. calculation of results, which represent relative concentrations of anti-dsDNA; and
k. determination of positive and negative results, whereby the lower limit is defined with the amount of added dsDNA.

For further understanding of the FIA method for detection of anti-dsDNA, according to the invention, reference should be made to the following detailed disclosure, taken in conjunction with the accompanying FIG. 1, which shows:

FIG. 1 A block-diagram of the protocol for antibody detection according to the invention.

Blood of patients with suspected autoimmune disease or confirmed SLE is collected and serum is prepared from it, so that the coagulated blood is centrifuged at 1800 xg for 10 minutes. Serum is much more appropriate for diagnostics than plasma, as the test background is much lower. At the same time, control sera are prepared, which are in the negative, medium positive and high positive range. These samples can be freshly prepared or previously stored samples and their values are determined with regard to the threshold value, which depends on the amount of added dsDNA.

Sera (samples and controls) are then decomplemented with incubation in a water bath for 30 minutes at 56° C. This step deactivates complement components, which could interfere with antibody detection.

Then, a suitable buffer solution is added to the serum. The buffer solution can be 100 to 200 mM borate buffer (pH between 7.0 and 9.0), and dsDNA. The latter can be from different sources. Preferably, the isolated dsDNA is from human venous blood, but may also be bacterial, bacteriophage, animal, plasmid or synthesized. In any case, it is important that the dsDNA conforms to recommended parameters, such as length ($10^5$ to $10^7$ bp), conformation, purity ($A_{260}/A_{280}$ ratio between 1.8 and 2), and suitably exposes the epitope recognized by anti-dsDNA. Final dsDNA concentration in samples is between 1 and 10 mg/L, preferably 1 mg/L. The most optimal comparability of results is achieved by adding 100 ng of DNA and 5 µL of serum to the sample. Formation of immune complexes is enabled with incubation in a water bath at temperature 37°

C. for 1 hour, followed by an additional incubation at 4° C., which can last between 0 and 24 hours, preferably 20 hours. An additional incubation in the cold is important to reach a dynamic equilibrium of the antigen—antibody (dsDNA anti—dsDNA) reaction.

Immune complexes are precipitated with addition of a saturated solution of ammonium sulfate or with a 3 to 8% PEG solution, wherein the samples are incubated 1 hour at 4° C. After incubation, the samples are centrifuged at 4° C. for 10 to 60 minutes, preferably for 15 minutes, at 400 to 2500 xg, preferably at 1800 xg. This allows the separation of immune complexes, which are in the precipitate, while the unbound dsDNA remains in the supernatant, as it cannot be precipitated with ammonium sulfate or PEG. The supernatant is carefully pipetted from the test tube, so that the precipitate remains intact. The samples are then heated to room temperature, which is generally from 22 to 26° C. This step is intended to optimize fluorescence measurements, so as to reduce or eliminate errors caused by the influence of sample temperature on measured fluorescence.

Both parts of the sample, the supernatant and the sample with precipitate, are labelled with a fluorescent dye, which is appropriate for detection and quantification of dsDNA, such as PicoGreen, Hoechst, SYBR Green, SYBR Gold, DAPI or Cy3. Preferably, PicoGreen is used, as it is well known as an effective dye for dsDNA. Separate labelling of the supernatant and sample with precipitate is intended to produce more precise and accurate results, since errors due to losses or system errors in measurements are thus avoided. This is particularly relevant in cases, in which results are marginally positive. The dye binds into the structure of dsDNA, regardless of whether it is bound with proteins (antibodies) or not. The dye PicoGreen has an excitation wavelength of 485 nm, and an emission wavelength of 520 nm. The labelling procedure is performed according to manufacturer's instructions. After labelling, the results are read fluorometrically, spectrophotometrically, with a Real-Time PCR instrument, flow cytometer or microscope. The detection method depends on the selected technique for the anti-dsDNA detection and thus also on the use of different laboratory materials (microtiter plates, test tubes, slides, etc.).

Test results, which represent the relative proportion of anti-dsDNA, are calculated according to the following formula:

$$\frac{\text{fluorescence } P - \text{fluorescence } S}{\text{fluorescence } P + \text{fluorescence } S}$$

in which fluorescence P is the fluorescence measured in the sample with precipitate and fluorescence S is the fluorescence measured in the supernatant.

Based on the results of healthy people, a threshold between a positive and a negative result has been determined at the concentration of added dsDNA in the range from 1 to 10 mg/L. If the result of the above given formula is above the threshold, the sample is positive. The threshold value depends on the ratio between the amount of added DNA and the used serum volume. At the added 100 ng of dsDNA and 5 µl of serum, the threshold value is 0.35. The test result is reliable, if the negative control and medium and high positive controls have appropriate values.

Results obtained with the FIA method, according to the invention have been compared to results obtained with already known and used methods. The analysis included 465 samples, which came to the laboratory for confirmation or exclusion of an SLE diagnosis. All samples have been analysed with three methods, namely standardized Farr-RIA method, CLIFT method and FIA method, according to the invention. Results are given in Table 1.

TABLE 1

Number of samples analysed with screening test CLIFT and confirmed with Farr-RIA method and FIA method according to the invention.

| | CLIFT | | | |
|---|---|---|---|---|
| | Positive | | Negative | |
| Confirmation methods | positive | negative | positive | negative |
| Farr-RIA | 22 | 41 | 0 | 402 |
| FIA method according to the invention | 37 | 26 | 3 | 399 |

As shown in Table 1, 63 positive and 402 negative samples have been determined with the CLIFT method, while 22 positive and 443 negative samples were determined with the Farr-RIA method. FIA method according to the invention showed 37 positive and 425 negative samples. When samples with CLIFT method were negative, the confirmatory test with the Farr-RIA method showed no positive samples. It can be seen from Table 1 that the FIA method according to the invention gave 3 false positive results, as there were 399 negative samples. Despite this small deviation, the reliability of the FIA method according to the invention is suitable, since the results show a 99% match. The CLIFT method showed 63 positive samples, but the Farr-RIA and FIA method according to the invention confirmed only 22 and 37 positive samples, respectively. Comparison of results obtained with the Farr-RIA method and the FIA method in the range of negative values is not applicable due to wide dispersion of results, which is a consequence of higher analytical sensitivity of the FIA method. Comparison of positive results obtained with the Farr-RIA method and the FIA method with Wilcoxon signed-rank test showed that there are no statistically significant differences between results obtained with both methods (p=0.24).

Embodiment I

Method according to the embodiment I is performed according to the following protocol. Samples and control sera are decomplemented for 30 minutes in a water bath at 56° C. 95 µL of 155 mM of borate buffer (pH 8), 5 µL of serum and isolated dsDNA to a final concentration of 1 mg/L are pipetted into glass tubes. Solutions are well mixed, tubes are tightly closed and incubated in a water bath at 37° C. for 1 hour, and then at 4° C. for 20 hours. After incubation 100 µL of a saturated solution of ammonium sulfate is added and mixed with a mixer. Then the tubes are incubated at 4° C. for 1 hour. After that, samples are centrifuged for 15 minutes at 4° C. at 1800 xg. After centrifugation, samples are heated to a temperature between 22 and 26° C. From 100 µL of supernatant, which has been carefully pipetted into a clean glass tube, 20 µL are pipetted into a microcentrifuge tube, into which 180 µL of working solution of fluorescent dye PicoGreen is added. The working concentration of the dye and its preparation are given in the manufacturer's instructions. From 100 µL of the remaining supernatant and precipitate, 20 µL of suspension is transferred to a second microcentrifuge tube, into which 180 µL of working solution of PicoGreen dye is added.

For calibration of the fluorometer, two standard solutions with a concentration of 0 and 10 mg/L and a final volume of 200 μL are prepared and measured.

Fluorescence of supernatant and samples with precipitate is measured with a fluorometer. Results are calculated according to the above given formula.

Embodiment II

Method according to the embodiment II is performed the same as in embodiment I up to the step of sample preparation for fluorescence measurements. Namely, samples and control sera are decomplemented for 30 minutes in a water bath at 56° C. 95 μL of 155 mM borate buffer (pH 8), 5 μL of sera and isolated dsDNA to a final concentration 1 mg/L are added into glass tubes. Solutions are well mixed, tubes are tightly closed and incubated in a water bath at 37° C. for 1 hour, and then for 20 hours at 4° C. After incubation, 100 μL of a saturated solution of ammonium sulfate are added to each tube and mixed. Then the tubes are incubated at 4° C. for 1 hour. After incubation, samples are centrifuged at 4° C. and 1800 xg for 15 minutes. After centrifugation, samples are heated to a temperature between 22 and 26° C. From 100 μL of supernatant, which has been carefully pipetted into a clean glass tube, 10 μL are pipetted into a microtiter plate appropriate for fluorescence measurements. To these samples 90 μL of working solution of fluorescent dye PicoGreen is added. From 100 μL of the remaining supernatant and precipitate, 10 μL of suspension is transferred into a microtiter plate and 90 μL of the working solution of PicoGreen dye is added. Fluorescence of the supernatant and sample with precipitate is measured spectrophotometrically, so that the excitation wavelength is 485 nm and emission wavelength is 520 nm, and the measurement lasts for 5 to 180 minutes. The aforementioned wavelengths are adjusted for the PicoGreen dye. Results are calculated according to the above given formula.

The described fluorometric immunoassay method for detection of anti-dsDNA for the purpose of serological diagnostics of autoimmune diseases according to the invention allows the use of chemicals that are less toxic for humans and the environment, which also leads to lower costs, as there is no need for special radioactive waste removal and additional personnel training for radioactive material handling. At the same time, the test results are equally reliable as the results obtained with the Farr-RIA method. In addition, results obtained with the FIA method according to the invention, are available to the physician in two days, in emergency cases even in one day, if the blood is collected in the morning. With this, all criteria for improvement of already known and accepted methods for detection of anti-dsDNA are fulfilled, as the fluorometric immunoassay method according to the invention is faster, cheaper and less dangerous for humans and the environment.

The invention claimed is:

1. A fluorometric immunoassay method for detecting antibodies against double-stranded DNA (anti-dsDNA), comprising
   providing decomplemented sera from a patient, providing isolated dsDNA as antigens from a source,
   Precipitating immune complexes with a saturated solution of ammonium sulfate or solution of polyethylene glycol (PEG), wherein the immune complexes are a consequence of incubation of decomplemented patient's sera with the dsDNA,
   separating the immune complexes into two samples,
   labeling the samples by adding fluorescent dyes specific to the dsDNA to the samples, and
   detecting of fluorescence in the samples, namely sample with supernatant and sample with precipitate, comprising immune complexes comprising dsDNA and anti-dsDNA,
   wherein the detected fluorescence is a consequence of binding of fluorescent dyes into the dsDNA.

2. The method according to claim 1 further comprising:
   a. providing decomplemented sera and control sera;
   b. isolating dsDNA from a suitable source;
   c. adding the isolated dsDNA and a buffer solution to the decomplemented sera to form a mixture;
   d. incubating the mixture to form immune complexes;
   e. precipitating the immune complexes with a saturated solution of ammonium sulfate or a 3 to 8% solution of polyethylene glycol (PEG);
   f. separating the precipitated immune complexes from unbound dsDNA with centrifugation to form two samples, namely sample with supernatant and sample with precipitate;
   g. heating the two samples to room temperature;
   h. labeling the two samples with a fluorescent dye specific to the dsDNA;
   i. measuring the samples' fluorescence;
   j. calculating results, which represent the relative concentration of anti-dsDNA in the samples; and
   k. determining positive and negative results, wherein the lower limit is defined with the amount of added dsDNA.

3. The method according to claim 1, wherein the dsDNA comprises dsDNA selected from the group consisting of human, animal, bacterial, bacteriophage, plasmid or synthesized dsDNA.

4. The method according to claim 1, wherein the final concentration of dsDNA in the sample comprises between 1 and 10 mg/L and the volume of added serum comprises between 0.05 and 50 μL.

5. The method according to claim 2, wherein the buffer solution consisting of 100 to 200 mM borate buffer with a pH comprising a value between 7.0 and 9.0.

6. The method according to claim 2, wherein the incubation of the mixture from step d lasts for 1 hour at 37 ° C., and comprises an additional incubation period for 0 to 24 hours.

7. The method according to claim 2, wherein the centrifugation step is done at temperature 4° C. for 10 to 60 minutes and at 400 to 2500 xg, and wherein the required temperature of heated samples after centrifugation is between 22 and 26° C.

8. The method according to claim 1, wherein the results are calculated so that the difference in fluorescence of the sample with precipitate and the supernatant is divided with the sum of fluorescence of the sample with precipitate and the supernatant, wherein the marginal result depends on the threshold value and all values above the threshold represent positive results.

9. The method according to claim 1, further comprising a step selected from the group consisting of monitoring of the course of autoimmune diseases.

10. The method according to claim 1, further comprising a step selected from the group consisting of monitoring the course of systemic lupus erythematosus (SLE).

11. A fluorometric immunoassay method for detecting antibodies against double-stranded DNA (anti-dsDNA), the method comprising Providing a sera specimen, isolated dsDNA as an antigen from a source, first and second containers, and a detector,
Adding the specimen to the first container,
Heating the specimen in the first container,
Adding a buffer solution to the specimen to form a mixture,
Adding the dsDNA to the mixture,
Incubating the mixture to form immune complexes,
precipitating the immune complexes in the first container,
incubating the mixture,
separating the mixture into
- a first sample comprising precipitates comprising immune complexes,
- a second sample comprising supernatants comprising unbound dsDNA, and transferring the second sample to a second container;
heating the first and second samples to room temperature,
adding fluorescent dye specific to dsDNA to the first and second samples,
detecting fluorescence in the first and second samples.

\* \* \* \* \*